(12) United States Patent
Yoshino

(10) Patent No.: US 7,298,815 B2
(45) Date of Patent: Nov. 20, 2007

(54) RADIOGRAPHIC INSPECTION APPARATUS AND RADIOGRAPHIC INSPECTION METHOD

(75) Inventor: Shinji Yoshino, Hyogo (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 0 days.

(21) Appl. No.: 11/482,064

(22) Filed: Jul. 7, 2006

(65) Prior Publication Data

US 2007/0009086 A1 Jan. 11, 2007

(30) Foreign Application Priority Data

Jul. 8, 2005 (JP) ............... 2005-199488

(51) Int. Cl.
*G01N 23/083* (2006.01)

(52) U.S. Cl. .......................... 378/25; 378/57

(58) Field of Classification Search ............... 378/57, 378/21–27, 68–69, 65
See application file for complete search history.

(56) References Cited

U.S. PATENT DOCUMENTS 5,848,115 A * 12/1998 Little et al. ............... 378/4
6,687,328 B2 * 2/2004 Bavendiek et al. ........... 378/58

\* cited by examiner

*Primary Examiner*—Hoon Song
(74) *Attorney, Agent, or Firm*—Steptoe & Johnson LLP.

(57) ABSTRACT

A radiographic inspection method of irradiating a circuit forming device with X-rays to inspect the inside of the device. The method includes an X-ray irradiation step of irradiating the circuit forming device with X-rays, an X-ray detection step of detecting X-rays having penetrated the circuit forming device which is rotated every predetermined degrees of angle about an axis intersecting the irradiation direction of X-rays at right angles, a tomogram creating step of creating a plurality of tomograms based on data on penetrated X-rays detected in the X-ray detection step, a projected image creating step of creating projected images in three axial directions intersecting at right angles based on the plurality of tomograms created in the tomogram creating step, and a defect detecting step of detecting a defect such as a crack of the circuit forming device based on the projected images created in the projected image creating step.

8 Claims, 7 Drawing Sheets

RADIOGRAPHIC INSPECTION APPARATUS AND RADIOGRAPHIC INSPECTION METHOD

FIELD OF THE INVENTION

The present invention relates to a radiographic inspection apparatus and a radiographic inspection method for inspecting a joint state inside a component mounted on a circuit forming device, to be specific a printed board, and a component packaged with resin or metal, or a joint state of a component mounted inside a printed board.

BACKGROUND OF THE INVENTION

Conventionally, methods for detecting a defect in a circuit forming device such as a printed board with radiation or X-rays for example, include a method of detection from an image obtained by two-dimensional image processing on an X-ray transparent image in one direction of a circuit forming device, or a method of detection from an image obtained by two-dimensional image processing performed separately on X-ray transparent images in two directions and three directions.

In such detection methods, however, the inside of a circuit forming device can be viewed only in a two-dimensional manner. Thus a defect cannot be correctly located, a blind spot appears in some three-dimensional shapes of the circuit forming device, or inspections are difficult in some regions, so that accurate detection of a defect cannot be expected.

In order to address the problem, a method using X-ray tomosynthesis (hereinafter, referred to as X-ray CT) is proposed. In this method, a plurality of consecutive tomograms are generated, a defective region considered to be within the range of predetermined threshold values relative to each tomographic plane are binarized and detected, and the region is numbered, so that the position of a defect, the size of a cuboid circumscribing the defect, and so on are measured (For example, Japanese Patent Laid-Open No. 1-297772, page 5, FIG. 3).

In a device for inspecting a defective foreign matter using this method, consecutive tomogram data created by X-ray CT is binarized for each tomogram based on a predetermined threshold value and regions are numbered, so that the position of a defect, the size of a cuboid circumscribing the defect, and so on are measured.

However, in the conventional device for inspecting a defective foreign matter, a long defect such as a crack intersecting a tomographic plane at right angles is reduced in size on the display and thus becomes hard to extract, and processing on a large number of tomographic planes results in a longer inspection time.

DISCLOSURE OF THE INVENTION

An object of the present invention is to provide a radiographic inspection apparatus and a radiographic inspection method so that even a long defect such as a crack intersecting a tomographic plane at right angles can be easily extracted with radiation and a test can be conducted in a short time.

In order to attain the object, a first invention is a radiographic inspection apparatus for irradiating an inspected object to inspect the inside of the object. The radiographic inspection apparatus comprises a holder for holding the inspected object, and rotating the object every predetermined degrees of angle about an axis intersecting an irradiation direction at right angles or swinging the object every predetermined degrees of angle about an axis placed in parallel with the irradiation direction, an irradiation device for irradiating the inspected object which is held by the holder and moved every predetermined degrees of angle, a radiation detector for detecting a radiation having penetrated the inspected object, a data storage device for storing data on the penetrated radiation detected by the radiation detector, a tomogram creating device for creating a plurality of tomograms based on the penetrated radiation data stored in the data storage device, a projected image creator for creating projected images in a plurality of directions based on the plurality of tomograms created by the tomogram creating device, and a defect detector for detecting a defect of the inspected object based on the plurality of projected images created by the projected image creator.

According to a second invention, the projected images created by the projected image creator of the radiographic-inspection apparatus are created for each of a plurality of projected planes intersecting at right angles.

According to a third invention, the projected image creator of the radiological inspection apparatus creates the projected images by setting a threshold value for the tomograms to extract therefrom parts corresponding to the defect, and adding the parts corresponding to the defect extracted based on the threshold value.

According to a fourth invention, the radiation used in the radiological inspection apparatus is one of an X-ray, a gamma ray, and a neutron ray.

A fifth invention is a radiographic inspection method of irradiating an inspected object to inspect the inside of the object. The radiographic inspection method comprises a radiation detection step of irradiating the inspected object and detecting a radiation having penetrated the object, the inspected object being rotated every predetermined degrees of angle about an axis intersecting an irradiation direction at right angles or the inspected object being swung every predetermined degrees of angle about an axis placed in parallel with the irradiation direction, a tomogram creating step of creating a plurality of tomograms based on data on the penetrated radiation, the radiation being detected in the radiation detection step, a projected image creating step of creating projected images in a plurality of directions based on the plurality of tomograms created in the tomogram creating step, and a defect detecting step of detecting a defect of the inspected object based on the projected images created in the projected image creating step.

According to a sixth invention, the radiation used in the radiological inspection method is one of an X-ray, a gamma ray, and a neutron ray.

According to the radiological inspection apparatus and the radiological inspection method, an inspected object is rotated or swung every predetermined degrees of angle, a plurality of tomograms are created using data on penetrated radiations such as an X-ray, a gamma ray, or a neutron ray on each moving position, projected images are created based on the tomograms in a plurality of directions, such as in three directions intersecting at right angles, and a defect is detected based on the projected images. Thus, based on the plurality of projected images, even a long defect such as a crack can be easily and positively detected in any direction.

Numerous characteristics and advantages of the present invention will be apparent from a preferred embodiment described in accordance with the accompanying drawings.

DESCRIPTION OF THE EMBODIMENT

The following will describe a radiographic inspection apparatus and a radiographic inspection method according to preferable embodiments of the present invention with reference to the accompanying drawings.

In the present invention, an inspection is performed using transparent images by radiation. In the specific embodiment, X-rays are used as the radiation.

In the present embodiment, an inspected object is a circuit forming device. To be specific, the inspected object is a printed board or an electronic component, or the combined or joined printed board and the electronic component. The printed board is applied to a single-sided substrate of paper phenol, a glass epoxy substrate with multiple layers, a film substrate, a substrate including an electronic component, and resin on which a circuit pattern is formed.

First, an X-ray inspection apparatus will be specifically described below as the radiographic inspection apparatus.

Figure 1:
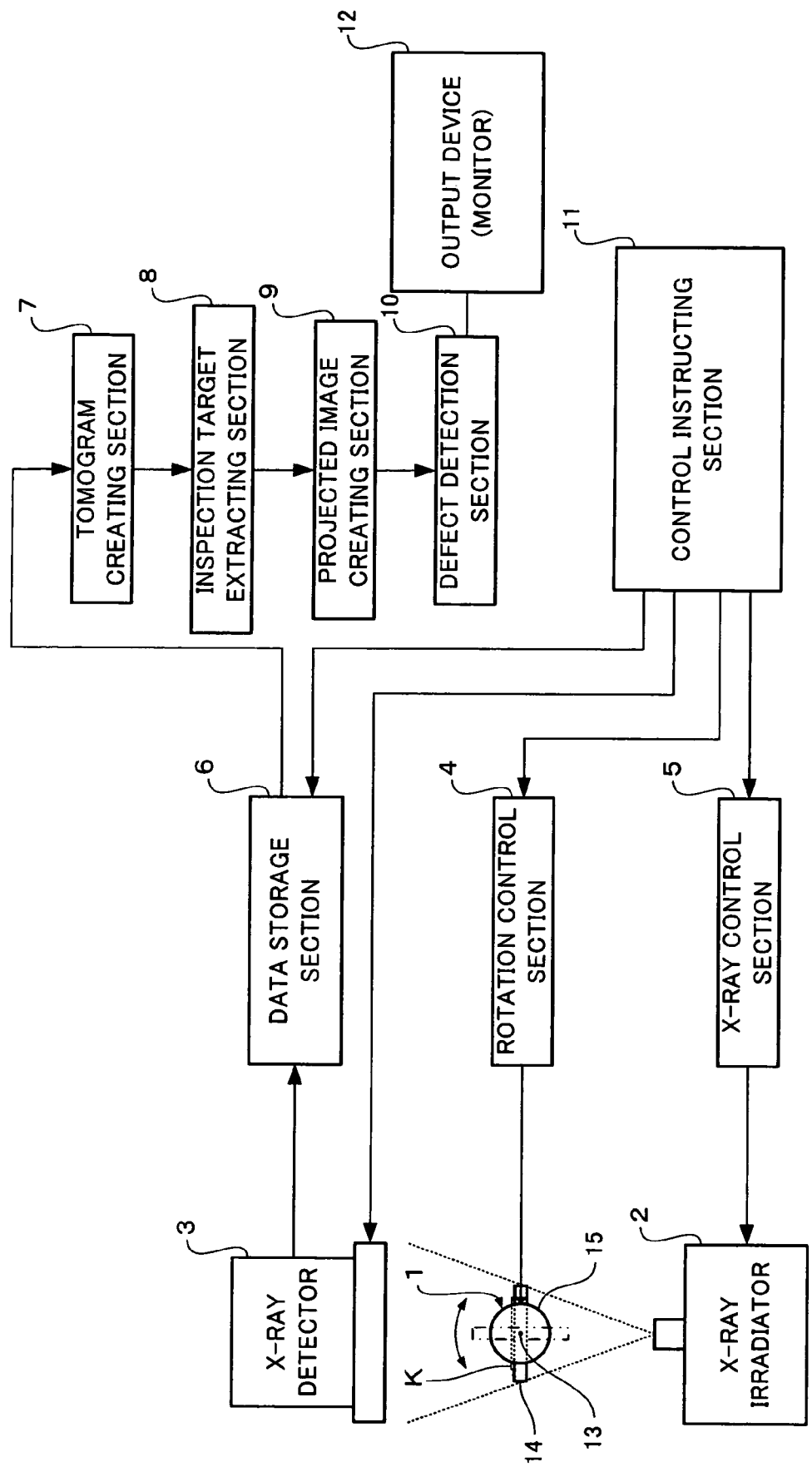
FIG. 1 is a block diagram schematically showing the configuration of a radiographic inspection apparatus according to an embodiment of the present invention.

The X-ray inspection apparatus comprises, as shown in FIG. 1, a holder 1 which holds a circuit forming device K serving as an inspected object such that the holder 1 rotates 360° about the axis intersecting the direction of X-ray irradiation at right angles, an X-ray irradiator (an example of an irradiation device) 2 for irradiating the circuit forming device held by the holder 1 with X-rays, an X-ray detector (an example of a radiation detector) 3 which is placed on a position corresponding to the X-ray irradiator 2 and detects X-rays passing through the circuit forming device held by the holder 1, a rotation control section (an example of a rotation controller) 4 for rotating (rotating and moving) the holder 1 every predetermined degrees of angle based on predetermined inspection data, an X-ray control section (an example of a radiation controller, also referred to as a radiation control section) 5 for instructing the X-ray irradiator 2 to generate X-rays, a data storage section (an example of a data storage device) 6 which is memory for storing data on penetrated X-rays, the X-rays being detected by the X-ray detector 3, a tomogram creating section (an example of a tomogram creating device) 7 for creating a plurality of tomograms from the data on penetrated X-rays stored in the data storage section, an inspection target extracting section (an example of an inspection target extractor) 8 which receives the a plurality of tomograms created by the tomogram creating section 7, specifies a range of tomograms to be inspected, and extracts the range, a projected image creating section (an example of a projected image creator) 9 for creating projected images in a plurality of directions, for example, three intersecting directions (the directions of X, Y and Z axes) from the range (part) extracted by the inspection target extracting section 8, that is, projected images on the XY plane, YZ plane, and ZX plane, a defect detection section (an example of a defect detector) 10 for detecting a defect of the circuit forming device based on the plurality of (three) projected images created by the projected image creating section 9, a control instructing section (an example of a control instructing device) 11 for outputting instruction signals to the constituent members 3 to 10 based on the predetermined inspection data (for example, X-ray intensity, angle data on the rotation of the holder, and so on), and an output device 12 such as a monitor which receives data on defects detected by the defect detection section 10 and displays the data in a predetermined display format. At least the tomogram creating section 7, the inspection target extracting section 8, the projected image creating section 9, the defect detection section 10, and the control instructing section 11 are implemented by programs (also acting as an arithmetic section) installed in a computer or implemented by devices with specialized functions.

The holder 1 is rotated every predetermined degrees of angle, for example, every two degrees or three degrees (the angle is not limited) while holding the circuit forming device K. To be specific, the holder 1 comprises a holding table (for example, the XY stage movable in two axial directions intersecting at right angles) 14 which is supported in a support frame so as to rotate about a predetermined axis (for example, horizontal axis) 13 and holds the circuit forming device K, and a motor 15 for rotating the holding table 14.

The X-ray irradiator 2 generates X-rays by colliding accelerated thermoelectrons with a target made of a predetermined material, and emits the X-rays. For example, any one of the following methods can be used: sealed tube method by which the inside is sealed almost in a vacuum all the time, and open tube method by which a filament for generating thermoelectrons can be replaced and the inside needs to be evacuated in each use of the filament. However, in order to increase an enlargement ratio and a resolution, it is desirable to minimize the focal size of an X-ray source, and thus in this device, open tube method is used with a focal diameter of 1 μm.

The X-ray detector 3 has the function of converting the dose of X-rays to an electric signal and uses an X-ray flat panel in which light converted by a scintillator, which converts X-rays to visible light, is directly incident on an optoelectronic transducer such as a CCD and a CMOS and converted to an electric signal. As with an X-ray image intensifier, after X-rays are converted by a scintillator which converts X-rays to charged particles, a magnetic field may be controlled to concentrate the charged particles, the charged particles may be collided with the scintillator and converted to visible light, and then the light may be converted to an electric signal by using an optoelectronic transducer such as a CCD and a CMOS.

Figure 2:
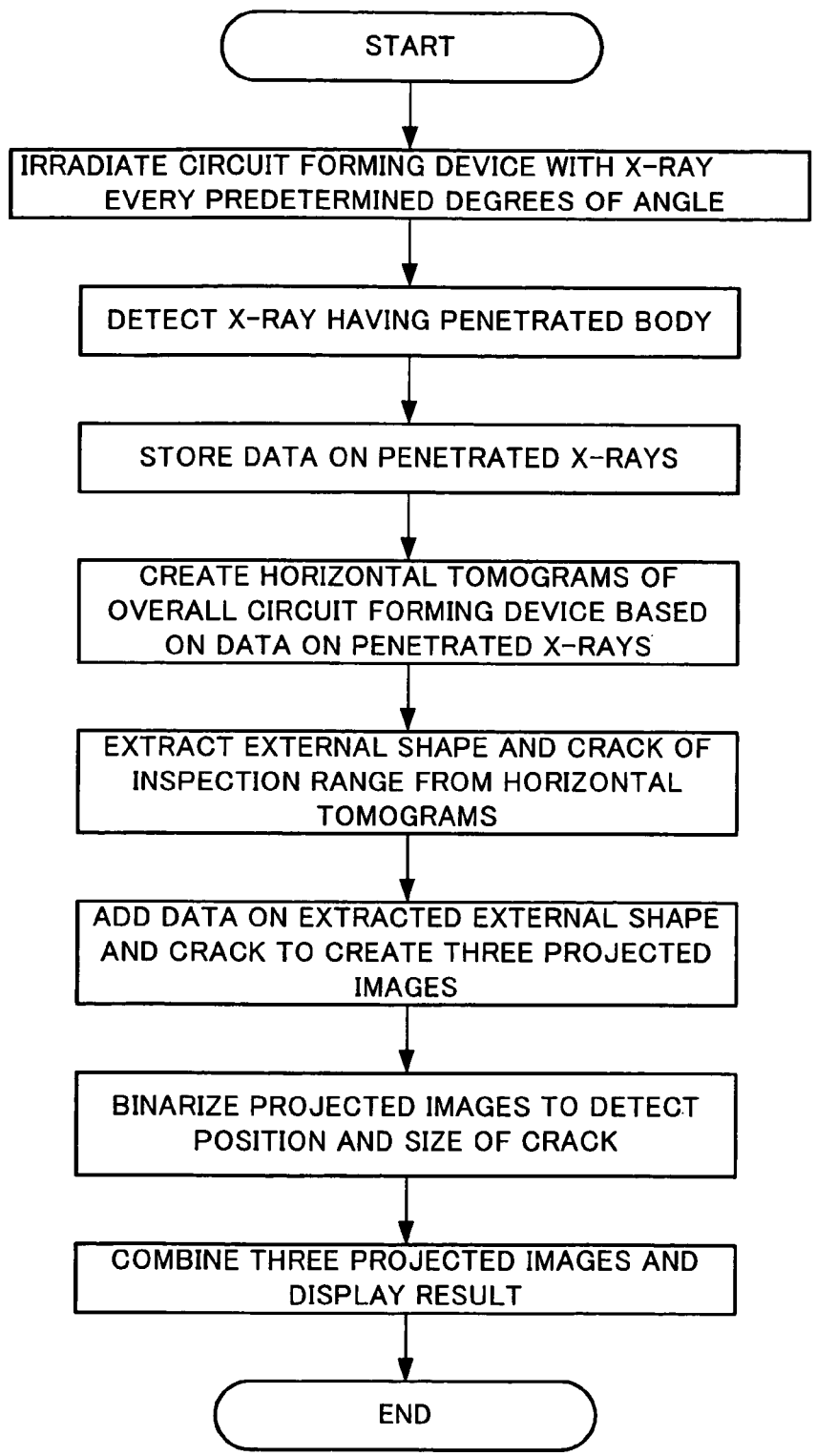
FIG. 2 is a flowchart for explaining the radiographic inspecting method according to the embodiment of the present invention.

Referring to the flowchart of FIG. 2, the following will discuss an X-ray inspection method of the circuit forming device.

First, the circuit forming device K to be inspected is held by the holder 1 in a predetermined position. And then, in response to an instruction from the control instructing section 11, the holder 1 and the X-ray irradiator 2 are operated via the rotation control section 4 and the X-ray control section 5, and the X-ray detector 3 is simultaneously operated.

In other words, the holder 1 which holds the circuit forming device K is rotated, for example, every two degrees or three degrees through 360° by the rotation control section 4, and X-rays are emitted on each rotation stop position (moving position) (an example of an irradiation step, also referred to as an X-ray irradiation step). As a matter of course, the control instructing section 11 provides the X-ray control section 5 with an instruction on predetermined voltage and current, so that X-rays with a predetermined intensity are outputted from the X-ray irradiator 2.

And then, an instruction for the rotation of the rotating shaft of the holder 1 is outputted to the rotation control section 4 and the holder 1 is stopped every two degrees. In synchronization with the stop, an irradiation signal is outputted to the X-ray irradiator 2 and an X-ray detection signal is outputted to the X-ray detector 3 (an example of a radiation detection step, also referred to as an X-ray detection step).

When the circuit forming device K is rotated 360° (one rotation) by the holder 1 and X-ray irradiation on the circuit forming device K is completed, 360 pieces of data on penetrated X-rays are detected by the X-ray detector 3 and stored in the data storage section 6 (data storing step).

Subsequently, the data on penetrated X-rays on all the irradiation positions (moving positions) in the data storage section 6 is inputted to the tomogram creating section 7, and a number of tomograms of the overall circuit forming device are created in a predetermined direction, for example, a number of horizontal tomograms are created (reconstructed by data processing) from the data on penetrated X-rays on all the irradiation positions (tomogram creating step). In other words, a number of images are created by horizontally slicing the overall circuit forming device at predetermined vertical intervals.

Figure 3A:
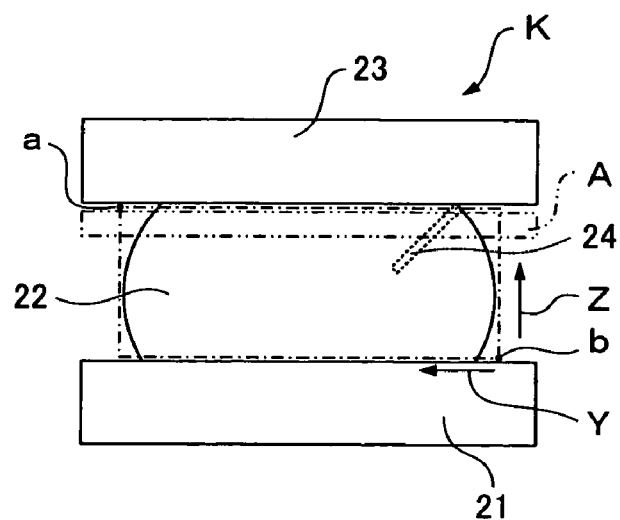
FIG. 3A is a side view showing a case where the radiographic inspection method is used for inspecting a circuit forming device.
Figure 3B:
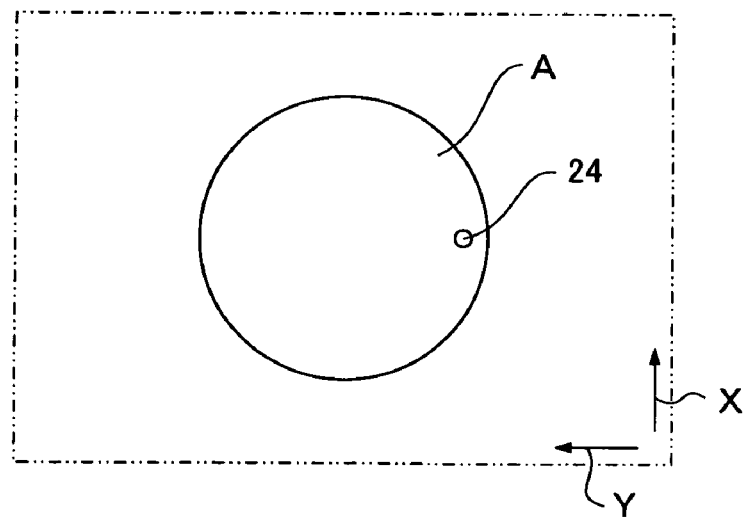
FIG. 3B is a horizontal sectional view showing a case where the radiographic inspection method is used for inspecting the circuit forming device.

For example, as shown in FIG. 3A, in the case of an inspection of a joint where a component package 23 is mounted on a printed board 21 via a spherical bump (BGA) 22 of solder or the like, that is, in the case of an inspection of the spherical bump 22, a number of horizontal tomograms (also referred to as sliced images) A are created vertically as shown in FIG. 3B. FIGS. 3A and 3B show that a needle-like crack (an example of a defect) 24 appears diagonally in the joint (spherical bump) 22.

Subsequently, the horizontal tomograms A created by the tomogram creating section 7 are inputted to the inspection target extracting section 8. In the inspection target extracting section 8, an inspection range is specified and the external shape of the inspection range and the crack 24 in the inspection range are extracted (defect extraction step)

For example, when specifying the joint 22, both end positions facing each other are specified to determine a range in the cross section. To be specific, as shown in FIG. 3A, coordinate a on an upper end and coordinate b on the lower end are specified.

And then, by pattern matching between the external shapes of the horizontal tomograms A of the specified joint 22 and the previously known circular external shapes of the spherical bump, the center position, radius, and so on are determined and extracted (instead of pattern matching, binarization and edge detection may be used). Image data (for example, data on lightness) inside the external shape of the extracted joint 22 is compared with a predetermined threshold value and only smaller values than the predetermined threshold value, for example, are extracted (larger values than the predetermined threshold value may be extracted for some kinds of image data) Thus, the external shape of the joint 22 and the crack 24 are extracted.

Figure 4A:
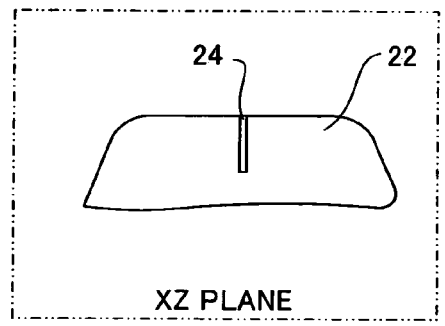
FIG. 4A is a projected view showing a case where the radiographic inspection method is used for inspecting a circuit forming device.
Figure 4B:
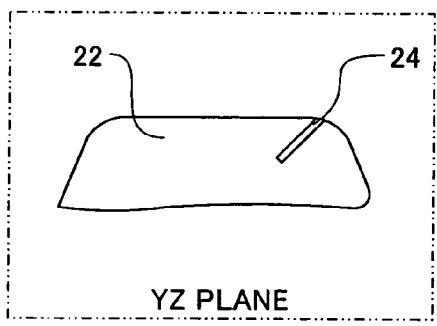
FIG. 4B is a projected view showing a case where the radiographic inspection method is used for inspecting the circuit forming device.
Figure 4C:
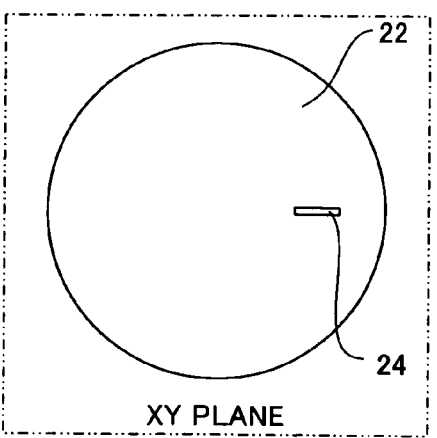
FIG. 4C is a projected view showing that the radiographic inspection method is used for inspecting the circuit forming device.

Subsequently, data on the external shape and crack 24 extracted by the inspection target extracting section 8 is inputted to the projected image creating section 9. In the projected image creating section 9, the data is added (also referred to as projected addition) along the X, Y and Z axes (three axial directions), so that three projected images shown in FIGS. 4A to 4C are created (projected image creating step).

Subsequently, the three projected images created by the projected image creating section 9 are inputted to the defect detection section 10 and binarized based on a predetermined threshold value to clarify the crack 24, and the region of the crack 24 is numbered, so that the position and size of the crack 24 are detected (defect detecting step). Finally, the position of the defect is determined among the three projected images and the result is displayed on the screen of the output device 12 such as a monitor (defect output step).

Figure 5:
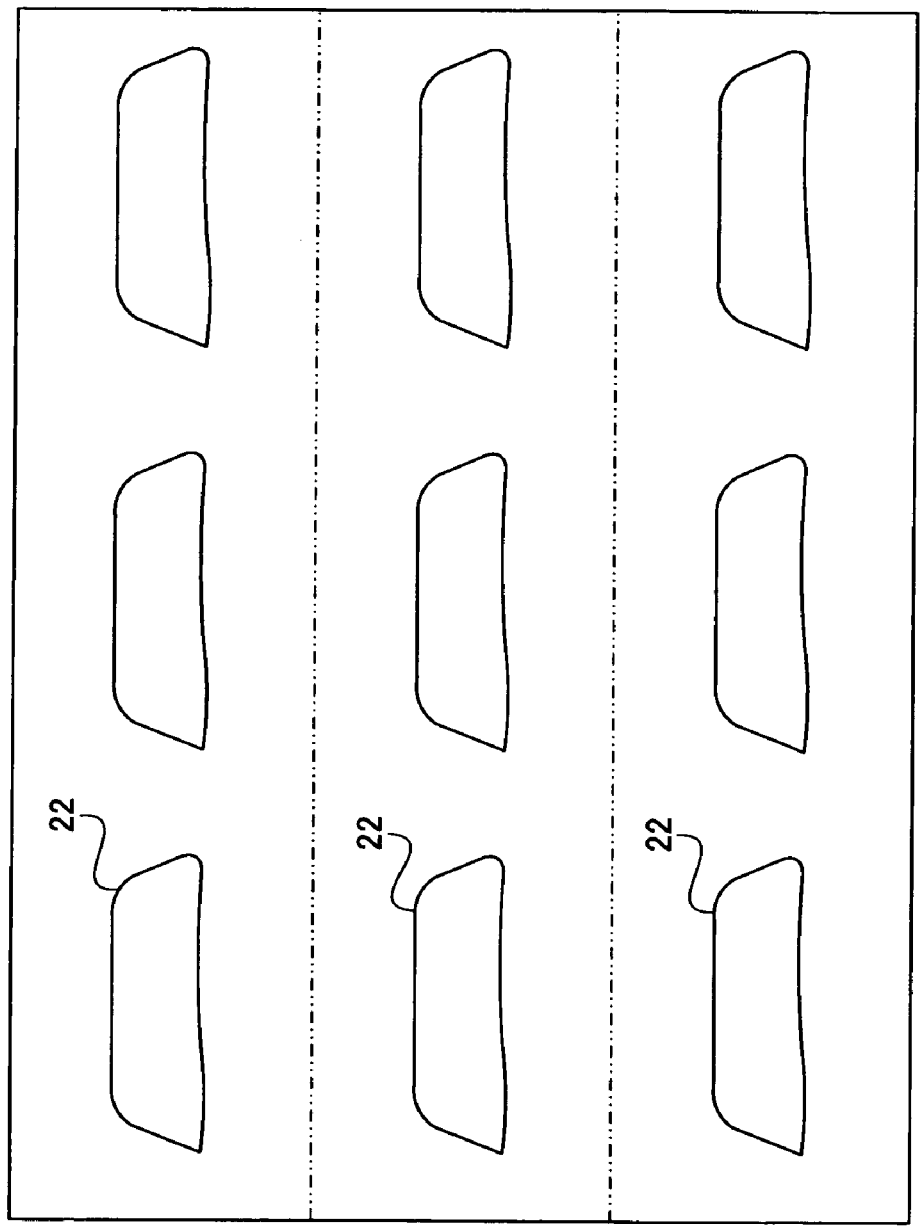
FIG. 5 is a projected view showing a variation of the radiographic inspection method.

The above explanation described the inspection of the single circuit forming device K. When a plurality of circuit forming bodies K (for example, nine circuit forming bodies K in three columns and three rows on the holding table) are inspected at a time, the projected images of all the circuit forming bodies K can be displayed at a time while being displaced with respect to each other as shown in FIG. 5.

According to the foregoing radiographic inspection apparatus and radiographic inspection method, a circuit forming device to be inspected is moved every predetermined degrees of angle to make a rotation, a plurality of tomograms are created using data on X-rays emitted and penetrated on each rotation stop position, external shapes and defects are extracted by performing data processing such as pattern matching and threshold processing on the tomograms, projected images in three directions intersecting at right angles are created using image data indicating the extracted defects, and the defects are detected based on the projected images. Thus even a long defect such as a crack can be easily and positively detected in any direction based on the plurality of projected images. According to the conventional method, in the case of a small defect in a tomogram intersecting the irradiation direction of X-rays at right angles, the defect cannot be easily detected.

According to the radiographic inspection apparatus and the radiographic inspection method, a defect can be detected in a shorter time as compared with detection on each tomogram.

In the present embodiment, the radiation is X-rays but gamma rays, neutron rays, and so on may be used. In this case, as a matter of course, a gamma-ray or neutron-ray irradiator, a gamma-ray or neutron-ray detector, and a gamma-ray or neutron-ray control section are used as the irradiation device, the radiation detector, and the radiation control section of the present embodiment.

Further, in the present embodiment, when a projected image is created, an external shape is extracted by pattern matching, image data inside the external shape is binarized according to a threshold value, and an addition is performed in a projected manner to create projection data. When a projected image is created, a standard deviation and the distribution among data of interest to be projected may be used as projection data, instead of the data binarized according to the threshold value. Thus even when target data is entirely changed, it is possible to obtain projection data not being affected by the change.

Before a projected image is created, Laplacian filtering may be performed on image data inside an external shape in order to enhance a defect and then subsequent processing may be performed.

In the present embodiment, a plurality of tomograms are created by rotating the circuit forming device about the axis intersecting the irradiation direction at right angles. For example, the circuit forming device may be rotated every predetermined degrees of angle (for example, 1 degree or 2 degrees) in a state in which the normal of the circuit forming device (a normal to a substrate surface) is tilted with respect to an axis placed in parallel with the irradiation direction. In other words, the holder may cause the normal of the circuit forming device to swing (so-called precession) relative to the axis placed in parallel with the irradiation direction.

Figure 6:
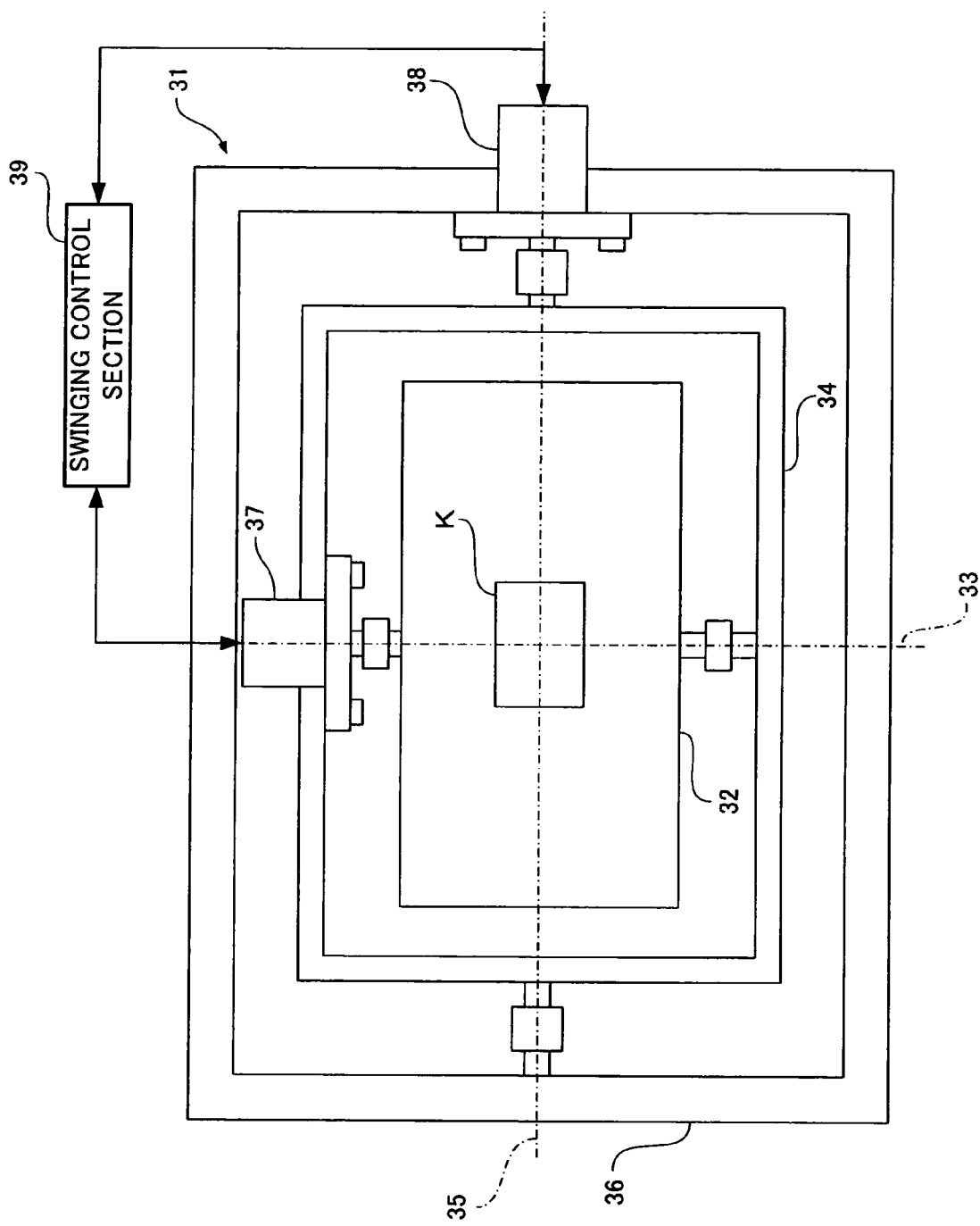
FIG. 6 is a plan view schematically showing a variation of a holder in the radiographic inspection apparatus.
Figure 7:
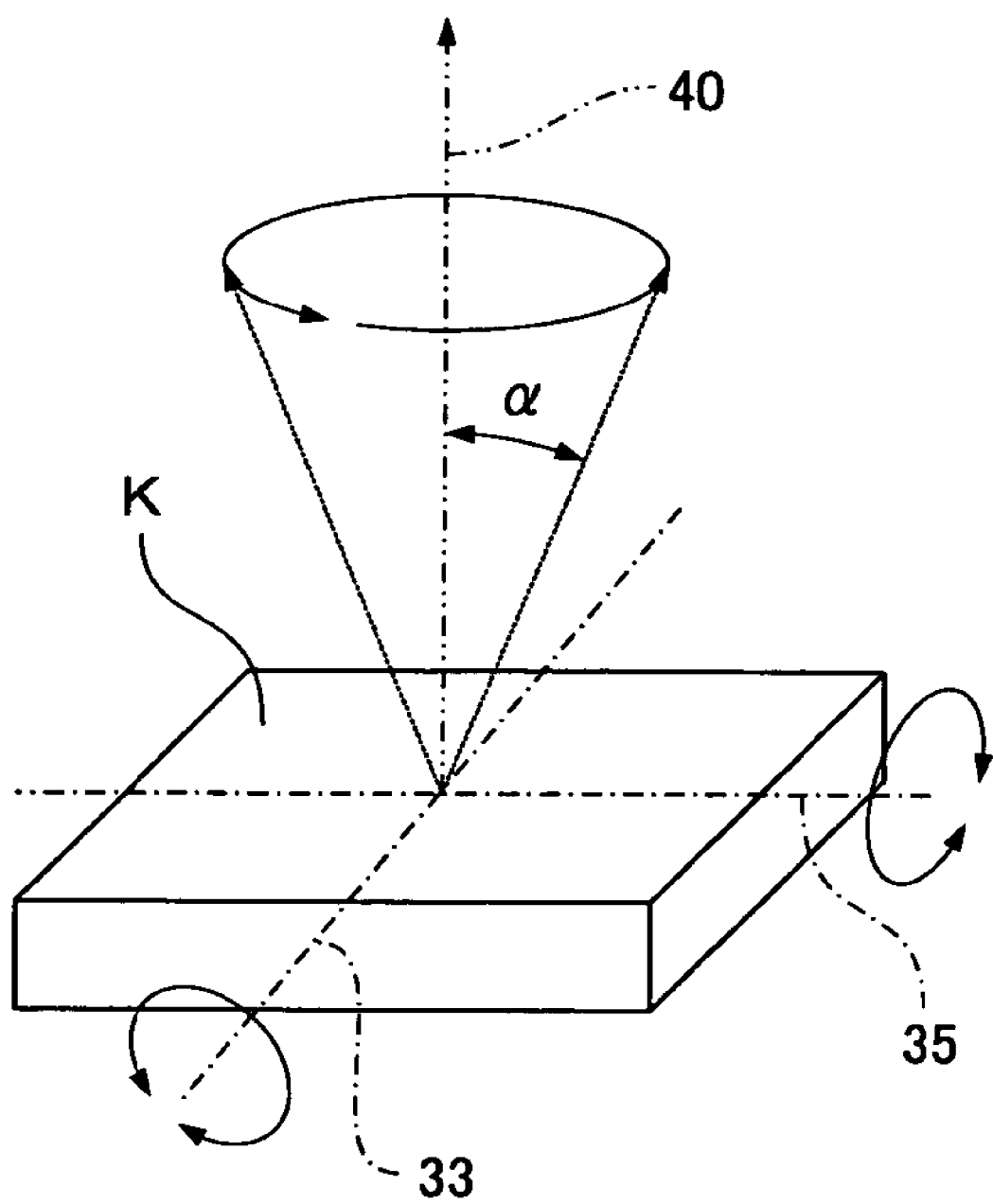
FIG. 7 illustrates operations of the holder in the variation.

Referring to FIGS. 6 and 7, the specific configuration of this case will be discussed below.

In this case, a holder (also referred to as a swinging device) 31 comprises a rectangular holding table (for example, an XY stage movable in two axial directions intersecting at right angles) 32 on which the circuit forming device K is placed, a rectangle inner frame 34 which holds the holding table 32 rotatably about a first axis (for example, the X axis) 33, a rectangular outer frame 36 which holds the inner frame 34 rotatably about a second axis (for example, the Y axis) 35 intersecting the first axis at right angles, a first motor 37 which is provided on the inner frame 34 to rock the holding table 32 about the first axis 33, and a second motor 38 which is provided on the outer frame 36 to rock the inner frame 34 about the second axis. The motors 37 and 38 are controlled in response to an instruction from the control instructing section 11 through a swinging control section 39.

To be specific, in response to an instruction from the control instructing section 11, the motors 37 and 38 are controlled through the swinging control section 39 such that as shown in FIG. 7, the holding table 32 swings at a predetermined angle a with respect to a third axis (for example, the Z axis) 40 intersecting the first axis 33 and the second axis 35 at right angles. In this state, photographing is performed using radiation.

Although a defect is detected from the three projected images in this embodiment, two projected images intersecting at right angles may be used to detect a linear defect. A linear defect affects more than a point-like defect, and the creation of two projected images results in shorter image processing time than the creation of three images.

What is claimed is:

1. A radiographic inspection apparatus which irradiates an object to inspect an inside of the object, the radiographic inspection apparatus comprising:
a holder which rotates the object a predetermined angle about an axis that intersects an irradiation direction at right angles or swings the object a predetermined angle about an axis that is parallel to the irradiation direction;
an irradiation device which irradiates the object;
a radiation detector which detects radiation that penetrates the object;
a data storage device which stores data on radiation detected by the radiation detector;
a tomogram creating device which creates a plurality of tomograms based on the radiation data stored in the data storage device;
a projected image creator which creates projected images in a plurality of directions based on the plurality of tomograms; and
a defect detector which detects a defect in the object based on the plurality of projected images.

2. The radiographic inspection apparatus according to claim 1, wherein the projected images created by the projected image creator are for a plurality of projected planes intersecting at right angles.

3. The radiographic inspection apparatus according to claim 1, wherein the projected image creator creates projected images by setting a threshold value for the tomograms to extract therefrom parts corresponding to the defect and adding the parts corresponding to the defect extracted based on the threshold value.

4. The radiographic inspection apparatus according to claim 1, wherein the radiation is one of an X-ray, a gamma ray, and a neutron ray.

5. A radiographic inspection method to irradiate an object to inspect an inside of the object, the radiographic inspection method comprising:
irradiating the object and
detecting a radiation that penetrates the object, which is rotated a predetermined angle about an axis that intersects an irradiation direction at right angles, or the object is swung a predetermined angle about an axis that is parallel to the irradiation direction,
creating a plurality of tomograms based on data from radiation that has penetrated an object,
creating projected images in a plurality of directions based on the plurality of said tomograms, and
detecting a defect of the object based on the plurality of projected images.

6. The radiographic inspection method according to claim 5, wherein the radiation is one of an X-ray, a gamma ray, and a neutron ray.

7. The radiographic inspection method according to claim 5, wherein the projected images created by the projected image creator are for a plurality of projected planes intersecting at right angles.

8. The radiographic inspection method according to claim 5, wherein the projected image creator creates projected images by setting a threshold value for the tomograms to extract therefrom parts corresponding to the defect and adding the parts corresponding to the defect extracted based on the threshold value.

* * * * *